(12) United States Patent
Martin et al.

(10) Patent No.: US 9,872,487 B2
(45) Date of Patent: *Jan. 23, 2018

(54) METHOD FOR PREPARING AN OPTIMUM DENSITY TERMITE BAIT COMPOSITION

(71) Applicant: BASF Corporation, Florham Park, NJ (US)

(72) Inventors: Jeffrey A. Martin, Manchester, MO (US); Ronald O. Richardson, Ellisville, MO (US)

(73) Assignee: BASF Corporation, Florham Park, NJ (US)

( * ) Notice: Subject to any disclaimer, the term of this patent is extended or adjusted under 35 U.S.C. 154(b) by 307 days.

This patent is subject to a terminal disclaimer.

(21) Appl. No.: 14/502,151

(22) Filed: Sep. 30, 2014

(65) Prior Publication Data

US 2016/0088843 A1 Mar. 31, 2016
US 2016/0286812 A9 Oct. 6, 2016

Related U.S. Application Data

(63) Continuation of application No. 13/725,207, filed on Dec. 21, 2012, now Pat. No. 8,881,448, which is a continuation of application No. 11/470,176, filed on Sep. 5, 2006, now Pat. No. 8,720,108, which is a continuation of application No. 10/059,564, filed on Jan. 29, 2002, now abandoned.

(51) Int. Cl.

| | |
|---|---|
| *A01N 47/34* | (2006.01) |
| *A01N 25/00* | (2006.01) |
| *A01N 25/34* | (2006.01) |
| *A01N 25/10* | (2006.01) |
| *A01M 1/02* | (2006.01) |
| *A01M 1/20* | (2006.01) |

(52) U.S. Cl.
CPC .......... *A01M 1/026* (2013.01); *A01M 1/2011* (2013.01); *A01N 25/006* (2013.01); *A01N 25/10* (2013.01); *A01N 25/34* (2013.01); *A01N 47/34* (2013.01); *A01M 2200/011* (2013.01)

(58) Field of Classification Search
None
See application file for complete search history.

(56) References Cited

U.S. PATENT DOCUMENTS

| | | | |
|---|---|---|---|
| 4,363,798 A | 12/1982 | D'Orazio | |
| 4,455,441 A | 6/1984 | Prestwich | |
| 4,582,901 A | 4/1986 | Prestwich | |
| 4,959,221 A | 9/1990 | Holmes | |
| 5,024,832 A | 6/1991 | Omata et al. | |
| 5,096,710 A | 3/1992 | Minagawa et al. | |
| 5,134,023 A * | 7/1992 | Hsu ........................ | B27N 3/007 264/109 |
| 5,141,744 A | 8/1992 | Chang et al. | |
| 5,152,992 A | 10/1992 | Kandathil et al. | |
| 5,300,293 A | 4/1994 | Minagawa et al. | |
| 5,564,222 A | 10/1996 | Brody | |
| 5,573,760 A | 11/1996 | Thorne et al. | |
| 5,637,298 A | 6/1997 | Stowell | |
| 5,695,776 A | 12/1997 | Ballard et al. | |
| 5,728,354 A | 3/1998 | Attygalle et al. | |
| 5,756,114 A | 5/1998 | Peterson | |
| 5,899,018 A | 5/1999 | Gordon et al. | |
| 5,921,018 A | 7/1999 | Hirose et al. | |
| 5,951,995 A * | 9/1999 | Adamoli, Jr. .......... | A01N 25/08 424/406 |
| 5,953,855 A | 9/1999 | Edwards | |
| 6,052,066 A | 4/2000 | Su | |
| 6,071,529 A | 6/2000 | Ballard et al. | |
| 6,093,389 A | 7/2000 | Galinis et al. | |
| 6,096,530 A | 8/2000 | Kato et al. | |
| 6,172,051 B1 | 1/2001 | Renello | |
| 6,202,342 B1 | 3/2001 | Edwards | |
| 6,203,811 B1 | 3/2001 | McPherson et al. | |
| 6,207,228 B1 | 3/2001 | Hundt et al. | |
| 6,235,301 B1 | 5/2001 | Ballard et al. | |

(Continued)

FOREIGN PATENT DOCUMENTS

| | | |
|---|---|---|
| CA | 1067401 A | 12/1979 |
| JP | 60100515 | 6/1985 |

(Continued)

OTHER PUBLICATIONS

Tablet (dictionary definition of tablet (Merriam-Webster http://www.merriam-webster.com/dictionary/tablet; on May 11, 2016 IDS).*
Non-Final Office Action for U.S. Appl. No. 13/725,207 dated Aug. 26, 2013; 11 pages.
JP 2001-335404 Machine translation accessed Aug. 17, 2013.
JP 2000-007516 Machine translation accessed Aug. 17, 2013.
Office action from European Application No. 10176835.6, dated Jan. 30, 2013.
Mirriam-Webster dictionary definition of tablet, accessed 20090511 on http://www.merriam-webster.com/dictionary/tablet.

(Continued)

*Primary Examiner* — Bethany P Barham
*Assistant Examiner* — Dominic Lazaro
(74) *Attorney, Agent, or Firm* — Armstrong Teasdale LLP

(57) ABSTRACT

A composition in compacted form for use for termite monitoring and control comprises a cellulose material which may be purified cellulose or micro-crystalline cellulose as a base bait, the composition being compacted to an optimum density of not less than approximately 1.033 g/cc. Also disclosed is a method for monitoring and controlling termite infestations which comprises the steps of a) preparing such a composition; b) placing the composition in a bait station; c) monitoring the station at periodic time intervals for termites; and d) upon observing termite infestation in the bait station, replacing the above composition with a bait composition containing a termite killing agent.

16 Claims, No Drawings

(56) References Cited

U.S. PATENT DOCUMENTS

| | | | |
|---|---|---|---|
| 6,287,596 B1 | 9/2001 | Murakami et al. | |
| 6,416,752 B1 | 7/2002 | Richardson et al. | |
| 8,720,108 B2 * | 5/2014 | Martin, Sr. | A01M 1/026 |
| | | | 424/405 |
| 8,881,448 B2 * | 11/2014 | Martin | A01M 1/026 |
| | | | 424/405 |
| 2001/0023552 A1 | 9/2001 | Fujimoto | |
| 2002/0018762 A1 | 2/2002 | Li | |

FOREIGN PATENT DOCUMENTS

| | | |
|---|---|---|
| JP | 61170390 A | 8/1986 |
| JP | 1143806 A | 6/1989 |
| JP | 1224307 A | 9/1989 |
| JP | 06205632 | 7/1994 |
| JP | 2000007516 A | 1/2000 |
| JP | 2000239114 A | 9/2000 |
| JP | 2001055301 A | 2/2001 |
| JP | 2001335404 A | 12/2001 |
| WO | 9928102 A1 | 6/1999 |
| WO | 0062610 A1 | 10/2000 |
| WO | 02052940 A1 | 7/2002 |

OTHER PUBLICATIONS

International Search Report from PCT/US03/01585 dated Jun. 11, 2003.

European Search Report for 03739668 dated Apr. 13, 2005, 3 pages.

* cited by examiner

METHOD FOR PREPARING AN OPTIMUM DENSITY TERMITE BAIT COMPOSITION

CROSS REFERENCE TO RELATED APPLICATIONS

This application is a continuation of application Ser. No. 13/725,207 filed on Dec. 21, 2012, which is a continuation of application Ser. No. 11/470,176 filed on Sep. 5, 2006, which is a continuation of application Ser. No. 10/059,564 filed on Jan. 29, 2002. The disclosure of application Ser. No. 13/725,207, and application Ser. No. 11/470,176, and application Ser. No. 10/059,564 is expressly incorporated herein by reference in their entireties.

BACKGROUND OF THE INVENTION

The present invention relates to compositions and methods for monitoring and controlling termite infestations and, more particularly, to such compositions and methods which provide bait compositions utilizing purified cellulose and/or micro-crystalline cellulose molded or compacted into desired shapes (e.g. tablets) with optimum density for increased bait loading capacity when placed in termite bait stations.

Termites are well known for their destructive effects on residences, businesses and various other structures. The damage from termite infestations results in huge economic losses, structural safety concerns, and destruction of architecturally valuable structures. Prior to the 1990's, the most widely accepted method to control termite infestation was to create a termite toxic barrier around the structure to be protected by digging trenches or boring holes at regular intervals and pumping in or injecting insecticide. While this method is often effective, physical circumstances, environmental sensitivity or other concerns make this method of control unsuitable at times. The technology of termite baiting was developed to overcome these disadvantages.

One strategy of the current termite baiting technology involves burying bait stations, usually some variation of a hollow tube with perforations and a removable top, around the perimeter of a structure at regular intervals of 8 to 10 feet for example, and adding some type of wood or cellulose to the station for bait or the monitoring matrix. The stations are then monitored for termites on a regular basis, e.g. on a monthly interval. When the wooden or cellulose bait is observed to be infested with termites, it is replaced with bait containing an active ingredient for killing or controlling the termites. Typically, the active containing bait is a paper or wood based product.

Since each bait station has to be placed underground, holes must be dug at regular intervals. Rocky and hardpan soils can make this operation very labor intensive and thus expensive. It is therefore desirable to make the insertion holes as small as possible. A hole size of approximately 2 inches or less in diameter is the most convenient size for current conventional one man power boring equipment. However, this 2 inch diameter hole size limits the amount of currently available wood or active bait that can be contained in the bait station. Currently available termite baits are not of optimum density due to air voids in the wood and paper product bait materials employed in the art. The bait loading capacity of current 2 inch bait stations therefore limits the time for monitoring and refilling the bait stations to approximately one month or less.

Substantial labor saving would be realized if the monitoring intervals could be extended to longer periods of time. Existing bait station designs having diameters of 4+ inches extend the monitoring time to 90 days, but installation requires the use of 4 inch post hole digging equipment. This in turn requires either large heavy equipment or very labor intensive manual post hole diggers. Both methods generate substantial amounts of soil excavated from the holes which requires disposal that adds to labor costs. The decreased labor costs for using such a larger bait station do not compensate for the costs of installation.

Another benefit from extended monitoring times is that since the station is not opened as frequently for monitoring, the termites are disturbed fewer times. It is believed that termites may abandon areas that are disturbed too often.

U.S. Pat. Nos. 5,096,710 and 5,300,293 are directed to bait compositions in tablet form which comprise as essential components (a) at least one insect-growth controlling agent; (b) dextrin with or without (c) a plant oil. Both of these patents specifically mention tableting pressures of about 10 to about 500 $kg/cm^2$.

There remains a need for improved bait compositions and methods which allow maximum bait weight to be loaded into termite bait stations to extend the monitoring time and reduce labor costs.

SUMMARY OF THE INVENTION

Among the several objects of the present invention may be noted the provision of a composition in compacted form for use for termite monitoring and control comprising a cellulose material as a base bait, the composition being compacted to an optimum density of not less than approximately 1.033 g/cc; the provision of such a composition preferably compacted to the form of a tablet; the provision of a composition which maximizes the amount of bait which may be loaded into a termite bait station; and the provision of a method for monitoring and controlling infestations through the use of such a composition in compacted form. Other objects will be in part apparent and in part pointed out hereinafter.

Briefly, the present invention is directed to a composition in compacted form for use for termite monitoring and control comprising a cellulose material selected from the group consisting of purified cellulose and microcrystalline cellulose as a base bait, the composition being compacted to an optimum density of not less than approximately 1.033 g/cc. The invention is further directed to a method for monitoring and controlling termite infestations comprising the steps of (a) preparing a composition in compacted form comprising a cellulose material selected from the group consisting of purified cellulose and microcrystalline cellulose, the composition being compacted to an optimum density of not less than 1.033 g/cc; (b) placing the composition in a bait station; (c) monitoring the station at periodic intervals for the presence of termites; and (d) upon observing termite infestation in the bait station, adding a bait composition containing a termite killing agent. The invention is also directed to a method for directly controlling termite infestations which comprises preparing a composition as above containing a termite killing agent and placing the composition in a bait station. Thus, protection begins as soon as the station is placed in the ground and with the optimum density, protection is afforded for longer periods than with current baits.

DESCRIPTION OF THE PREFERRED EMBODIMENTS

In accordance with the present invention, it has now been found that by compacting a composition comprising purified cellulose or microcrystalline cellulose as a base bait to an optimum density of not less than approximately 1.033 g/cc, maximum loading of termite bait stations may be achieved resulting in an extension of the time period needed for monitoring and refilling the bait stations. Through the practice of the present invention, improvements in current termite bait application practices are realized by first processing the termite base bait composition into custom physical forms, such as tablet forms, with optimum densities of not less than 1.033 g/cc which permits bait compositions shape and form versatility and substantially greater loading of monitoring and control bait into current commercially available termite bait stations than current commercial baits. As can be seen from the tableting studies presented hereinafter, the optimum compaction/density parameters for the compositions of the invention include a density of approximately 1.196 g/cc, an area compaction pressure of 688.71 kg/cm$^2$, a compaction pressure of 10,000 lbs. and a compaction ratio of 3.32.

In carrying out the practice of the invention, a composition in compacted form is prepared, the composition comprising a cellulose material which may be purified cellulose or microcrystalline cellulose. The cellulose material may be a microcrystalline cellulose in powdered form sold under the trade designation "Lattice NT-020 Microcrystalline" cellulose having an average particle size of 20 micrometers (FMC Corporation) or noncrystallized cellulose sold under the trade designation "Solka Floc" (International Fiber Corp.) having an average particle size in the range of 20 to 100 micrometers. Other brands of purified cellulose or microcrystalline cellulose may also be employed in the practice of the invention. The cellulose composition is compacted into tablets, briquets, pellets, spikes, granules or extruded forms which may be made by tablet presses, roller compaction or other means known to those skilled in the art.

A product such as TC-223 Termite Bait Powder (0.25% dimilin (diflubenzuron) and the balance being "Lattice NT-020" or "Solka Floc" cellulose) is generally well suited to termite ingestion and provides maximum termite contact due to its fine particle size. However, the one disadvantage it has is low bulk density which limits the amount that can be loaded into a bait station tube to a maximum of 27 grams with conventional packaging equipment. Termite feed rates studies in a laboratory termite colony indicate that the ingestion of 9 grams per week of the TC-223 formulation base is a reasonable estimate. While in real world situations this rate will vary dramatically due to influences such as termite species, termite population size, alternate food sources, weather conditions etc., the rate of 9 grams per week is used for illustration purposes. At this rate, a conventional bait station tube filled with 27 grams of TC-223 Termite Bait Powder would be emptied in three weeks, substantially less than the standard one month time used for monitoring the bait and replacing the empty bait tube. In accordance with the present invention, the monitoring interval of, for example, 10 weeks may be extended to 11 weeks by utilizing a compacting pressure of 10,000 lbs., to 12 weeks by utilizing a pressure of 15,000 lbs. and to 13 1/2 weeks by utilizing a pressure of 20,000 lbs.

If the cellulose material employed is in powder form rather than granule form, it must be deaerated either prior to compacting or during compacting to prevent "capping" which is a condition where a lamination of the tablet occurs when pressure is suddenly released after the compaction process. Powder contains a large amount of air which is compressed rather than vented during compaction. When the pressure is released, the air returns to its original volume causing cracks or laminations in the tablets.

In addition to the cellulose material, the composition of the invention for use for termite monitoring and control may also contain additional termite attractants and/or pheromones. Any termite attractants known to those skilled in the art may be used such as paper and other forms of cellulose.

Once the monitoring of the bait station confirms the presence of termites, the composition in the bait station is then filled with a bait composition containing a termite killing or controlling agent or termiticide. Any known termite killing or controlling agent or termiticide can be used in the practice of the invention. These include chitin synthesis inhibitors such as hexaflumuron, flufenoxuron, lufenurin and diflubenzuron (dimilin), juvenile hormone mimics such as methoprene and pyriproxyfen, stomach toxicants such as sulfuramide, abamectin, cryolite, boric acid and alkali and alkaline earth salts of boric acid, and contact insecticides such as thiamethoxam, imidicloprid and fipronil, or mixtures or combinations of these agents. The termite killing or controlling agent may be present in the bait composition in various concentrations such as 0.01 to 10% by weight.

The following examples illustrate the practice of the invention

Example 1

A Carver Model 3889 15 Ton Press equipped with the standard 1.125 inch inside diameter test mold kit was utilized to test various compaction characteristics and formulation parameters. The Carver Press employed was not equipped with heated platens on the jaws.

The standard mold produces a tablet which fits nicely into a standard bait tube (1 1/4" inside diameter). The tube will hold 5 or more tablets depending upon the tablet height. Tablet height is a function of formulation weight, physical form (powder or fine granule) and compaction pressure. The formulation weight was kept constant at 15 grams per compaction test during the evaluation. Both TC-223 powder and fine granulation were evaluated through several compaction pressures. De-aeration of the powder was accomplished by filling the mold with 10 grams of powder, placing the upper punch into the mold and lightly pressing the powder by hand to force out the air. The remaining 5 grams then fit into the mold. Tablet diameter and height were measured and volumes and densities calculated.

Compaction pressures of 3300, 7500, 10000, 15000 and 20000 lbs. were tested on powder and fine granulation formulations of TC-223. Both formulations were taken from pilot tests using a 10 cu. ft. Marion Mixer.

The results are summarized in the following table:

| Material | Tablet Weight (gm) | Diameter (cm) | Area (cm$^2$) | Tablet Height (cm) | Mold Volume (cc) | Tablet Volume (cc) | Density (g/cc) | Compaction Ratio | Tableting Pressure in Pounds | Tableting Pressure Kg/cm$^2$ | Tube Loading Multi Tabs Calc. (gms) | Comments |
|---|---|---|---|---|---|---|---|---|---|---|---|---|
| Tablet From Fine Granule NT-200 | 15 | 2.9 | 6.6 | 2.6 | 41.59 | 17.16 | 0.874 | 2.42 | 3300 | 227.21 | 80.19 | Too soft, Low Loading |
| Tablet From Fine Granule NT-200 | 15 | 2.9 | 6.6 | 2.2 | 41.59 | 14.52 | 1.033 | 2.86 | 7500 | 516.53 | 94.77 | Fair hardness, Fair Density |
| Tablet From Fine Granule NT-200 | 15 | 2.9 | 6.6 | 1.9 | 41.59 | 12.54 | 1.196 | 3.32 | 10000 | 688.71 | 109.77 | Hard, Good loading |
| Tablet From Fine Granule NT-200 | 15 | 2.9 | 6.6 | 1.75 | 41.59 | 11.55 | 1.299 | 3.60 | 15000 | 1033.06 | 119.18 | Very Hard, Excell. Loading |
| Tablet From Fine Granule NT-200 | 15 | 2.9 | 6.6 | 1.65 | 41.59 | 10.89 | 1.377 | 3.82 | 20000 | 1377.41 | 126.36 | Very Hard, Max. Loading |
| Tablet From Deaerated Powder | 15 | 2.9 | 6.6 | 1.9 | 41.59 | 12.54 | 1.196 | 3.32 | 15000 | 1033.06 | 109.74 | Hard, Good Loading |
| Tablet From Deaerated Powder | 15 | 2.9 | 6.6 | 1.7 | 41.59 | 11.22 | 1.337 | 3.71 | 20000 | 1377.41 | 122.65 | Hard, Excel. Loading |
| Tablet From Deaerated Powder | 15 | 2.9 | 6.6 | 2.1 | 41.59 | 13.86 | 1.082 | 3.00 | 10000 | 688.71 | 99.29 | Fair hardness, Fair Density |
| Tablet From Deaerated Powder | 15 | 2.9 | 6.6 | 2.3 | 41.59 | 15.18 | 0.988 | 2.74 | 7500 | 516.53 | 90.65 | Fair hardness, Marginal Loading |
| Tablet From Deaerated Powder | 15 | 2.9 | 6.6 | 2.7 | 41.59 | 17.82 | 0.842 | 2.33 | 3300 | 227.27 | 77.22 | Too soft, Low Loading |
| Bayer Tube Calculated Tablet Volume | | 2.9 | | 13.9 | | 91.77 | | | | | | |
| Bayer Tube Calculated Fine Granule Vol. Fill | | | | | | 110.8 | 0.361 | | | 40.00 | | |

From the table, it can be seen that optimum compacting characteristics were associated with the fine granulation formulation and that 7500 lb. compaction pressure on the granule formulation appears to be the lower limit for obtaining an acceptable density tablet. Using the assumed 9 grams per week termite ingestion number, enough bait could be added to last approximately 10½ weeks. The desired monitoring time is at least 12 weeks (3 months). Increasing the compaction pressure to 10,000 lbs. using the fine granule formulation tableted well and gave a much denser tablet with an approximate calculated monitoring time of the desired 12 weeks. Compaction pressures of 15,000 lbs. and 20,000 lbs. using the fine granule formulation, again both tableted well and extended the monitoring time to 13 weeks and 14 weeks respectively.

Based upon the results set forth in the above table, the optimum compaction/density parameters appear to be 10,000 lbs. compaction pressure, a density of 1.196 gm/cc, a compaction ratio of 3.32 and an area compaction pressure of 688.71 kg/cm$^2$.

Example 2

The following bait composition was prepared for tableting:

| Dimilin | 5.56 grams |
|---|---|
| Solka Floc granules | 94.44 grams |

40 gram slug tablets were made using the Carver Press with 2.25" diameter die at 20,000 lbs. tableting pressure. The "slugs" were then ground in a hand grist mill to granules. The granules were shifted to 12/20 and 20/45 mesh sizes. Overs were hand ground through a 12 mesh screen with a pestle. The 20/45 mesh granules were than tableted into 5 gram 1.25" diameter tablets using the Carver Press at 10,000 tableting pressure.

In view of the above, it will be seen that the several objects of the invention are achieved and other advantageous results attained.

As various changes could be made in the above methods and compositions without departing from the scope of the invention, it is intended that all matter contained in the above description and shown in the accompanying drawings shall be interpreted as illustrative and not in a limiting sense.

What is claimed is:

1. A method for preparing an extruded composition for use for termite monitoring and control, the method comprising extruding a composition comprising a cellulose material and an active ingredient for killing or controlling termites to a density of not less than 1.033 g/cc.

2. A method as set forth in claim 1 wherein said cellulose material is purified cellulose.

3. A method as set forth in claim 1 wherein said cellulose material is micro-crystalline cellulose.

4. A method as set forth in claim 1 wherein said active ingredient for killing or controlling termites is selected from the group consisting of chitin synthesis inhibitors, juvenile hormone mimics, stomach toxicants, contact insecticides and mixtures thereof.

5. A method as set forth in claim 4 wherein said synthesis inhibitor is selected from the group consisting of hexaflumuron, flufenoxuron, lufenurin, and dimilin.

6. A method as set forth in claim 1 wherein said active ingredient for killing or controlling termites is present in the extruded composition in a concentration from 0.01% to 10% by weight.

7. A method as set forth in claim 1 wherein said extruded composition additionally contains a termite attractant and/or pheromone.

8. A method as set forth in claim 1 wherein said extruded composition has a density of 1.196 g/cc.

9. A method for controlling termite infestations comprising the steps of:

(a) compacting a composition comprising a cellulose material and an active ingredient for killing or controlling termites by extrusion to a density of not less than 1.033 g/cc; and
(b) placing said extruded composition in a bait station.

10. A method as set forth in claim 9 wherein said cellulose material is purified cellulose.

11. A method as set forth in claim 9 wherein said cellulose material is micro-crystalline cellulose.

12. A method as set forth in claim 9 wherein said active ingredient is selected from the group consisting of chitin synthesis inhibitors, juvenile hormone mimics, stomach toxicants, contact insecticides and mixtures thereof.

13. A method as set forth in claim 12 wherein said synthesis inhibitor is selected from the group consisting of hexaflumuron, flufenoxuron, lufenurin, and dimilin.

14. A method as set forth in claim 9 wherein said active ingredient for killing or controlling termites is present in the extruded composition in a concentration from 0.01% to 10% by weight.

15. A method as set forth in claim 9 wherein said extruded composition additionally contains a termite attractant and/or pheromone.

16. A method as set forth in claim 9 wherein said extruded composition has a density of 1.196 g/cc.

\* \* \* \* \*